United States Patent [19]

Balint, Jr.

[11] Patent Number: 5,075,423
[45] Date of Patent: Dec. 24, 1991

[54] PURIFICATION OF PROTEIN A BY AFFINITY CHROMATOGRAPHY FOLLOWED BY ANION EXCHANGE

[75] Inventor: Joseph P. Balint, Jr., Seattle, Wash.

[73] Assignee: Imre Corporation, Seattle, Wash.

[21] Appl. No.: 471,014

[22] Filed: Jan. 24, 1990

Related U.S. Application Data

[63] Continuation of Ser. No. 223,183, Jul. 22, 1988, abandoned.

[51] Int. Cl.$^5$ .................... C07K 3/18; C07K 3/22; C07K 3/28; C07K 15/04
[52] U.S. Cl. .................................... 530/350; 530/413; 530/416
[58] Field of Search .................... 530/413, 416, 350

[56] References Cited

FOREIGN PATENT DOCUMENTS

| | | |
|---|---|---|
| 0107509 | 5/1984 | European Pat. Off. . |
| 0282308 | 9/1988 | European Pat. Off. . |
| 0289129 | 11/1988 | European Pat. Off. . |
| 2205530 | 5/1974 | France . |
| 84/00773 | 3/1984 | PCT Int'l Appl. . |
| 1447074 | 11/1973 | United Kingdom . |

OTHER PUBLICATIONS

Edwin et al., 1986, Applied and Environmental Microbiology 52(6):1253–1257.
Pharmacia 1986, Separation News, vol. 136, Serial No. 50-01-339, pp. 1–8.
Seki et al., 1985, Microbiol Immunol. 29(6):559–563.
Sjoholm et al., 1973, J. Immunol. 110(6):1562–1569.
Fluer, F. S., Nov. 1983, Dialog File 155 Accession No. 84100308, Zh Mikrobiol Epidemid Immunobiol, pp. 36–41.
Schrezenmeier et al., 1987, Biosir No. 85037909, J. Immunol. Methods 105(1):133–138.
Mueller et al., 1973, Chemical Abstracts No. 56026y, Pesqui. Agropecu. Bras. Ser. Vet. 8:115–119.
Sofer, G., 1984, Bio/Technology, Dec., pp. 1035–1038.
Sofer, G., et al., 1983, *BioTechniques*, Nov./Dec., pp. 198–203.
Scopes, R. K., *Protein Purification*, N.Y., Springer-Verlag, 1982, pp. 67–101.
Carlsson, R., et al., 1984, Cellular Immunology, 86:136–144.
Smith et al. (1983), J. Immunol. 130:773.
Hudson and Hay, Practical Immunology, 2nd. ed., Blackwell Scientific Publications, Oxford, 1980, pp. 169–175.
Schrezenmeier et al. (1987), J. Immunol. Meth. 105:133–137.
Sjoquist et al. (1972) Eur. J. Biochem. 29:572–578.
Balint, Jr., et al. (1989), J. Immunol. Meth. 116:37–43.

*Primary Examiner*—Margaret Moskowitz
*Assistant Examiner*—Keith C. Furman
*Attorney, Agent, or Firm*—Townsend and Townsend

[57] ABSTRACT

Affinity-purified protein A preparations are contacted with a suitable anionic exchange material in order to remove trace contamination. Staphylococcal enterotoxin B (SEB) and other proteinaceous contaminants are removed by passing such affinity-purified protein A preparations through a DEAE-cellulose column and thereafter selectively eluting the protein A to separate the contaminants. Very high purity protein A composition are thus obtained, typically having a contaminant concentration of about 5 weight % or below, with below about 0.001 weight % SEB.

15 Claims, 2 Drawing Sheets

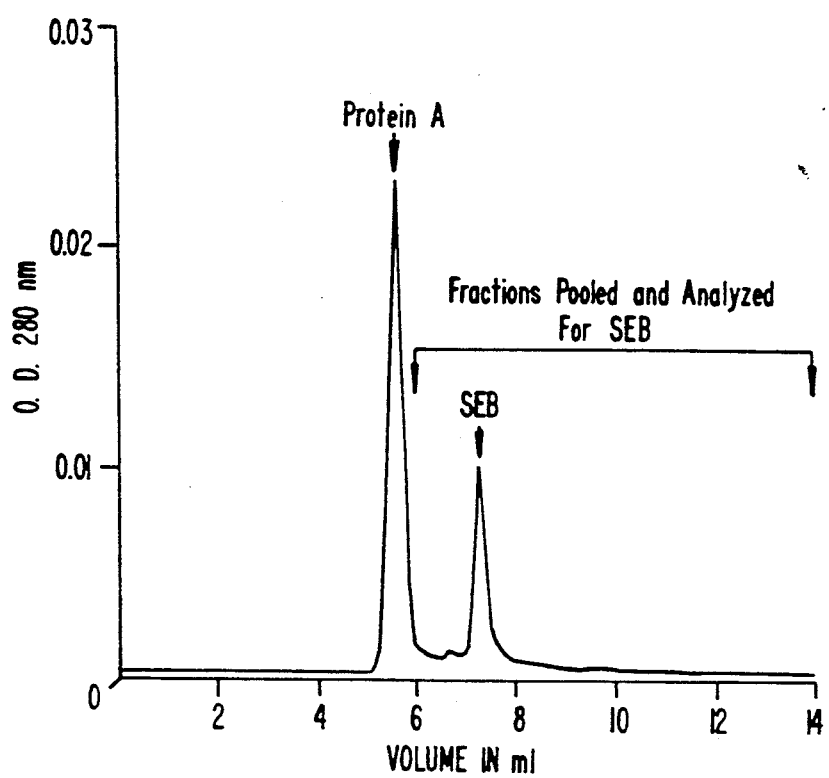
FIG._1.
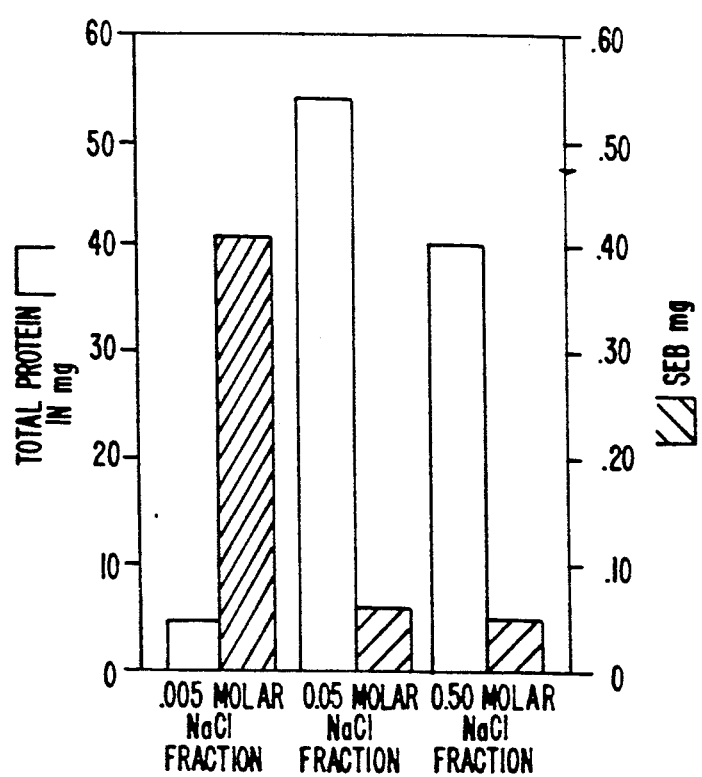
FIG._2.

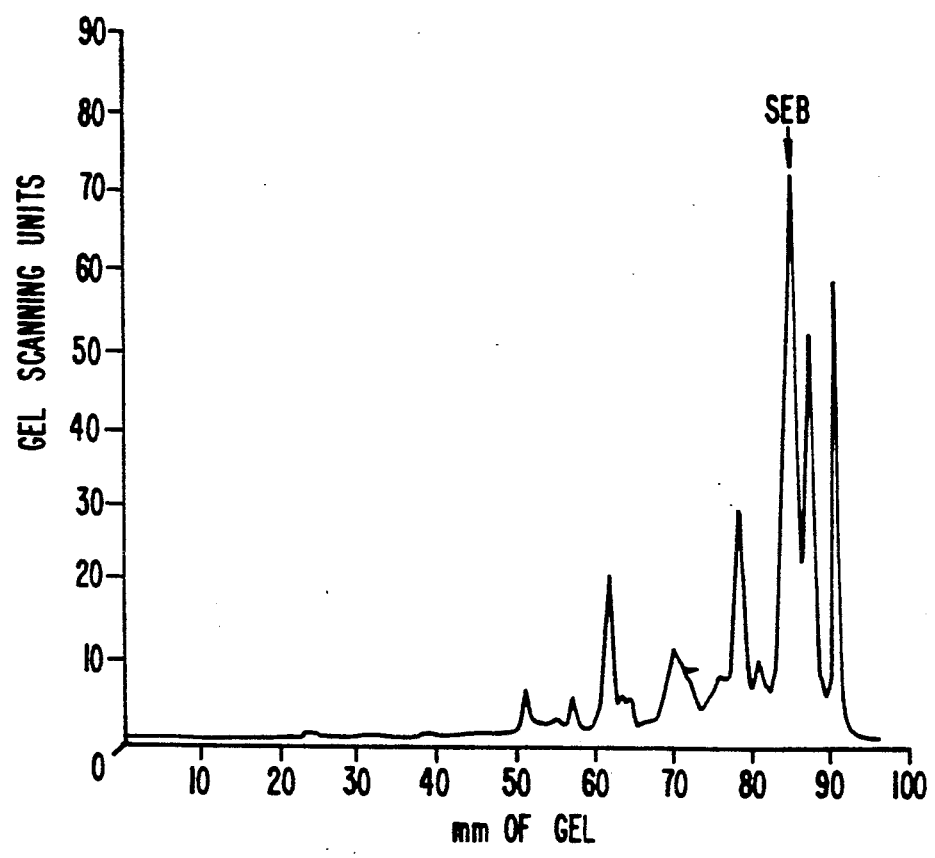
FIG._3.

PURIFICATION OF PROTEIN A BY AFFINITY CHROMATOGRAPHY FOLLOWED BY ANION EXCHANGE

This is a division of application Ser. No. 07/223,183, filed July 22, 1988, now abandoned.

BACKGROUND OF THE INVENTION

1. Field of the Invention

The present invention relates generally to purified protein A compositions and methods for the production of such compositions. In particular, the present invention relates to methods for removing enterotoxins and other contaminants from affinity-purified protein A compositions.

Protein A is a cell surface protein which can be isolated from particular strains of *Staphylococcus aureus* and which is able to bind free IgG and IgG-complexes. IgG-complexes are antigen-IgG complexes which circulate in patient serum and are not removed by the normal phagocytic mechanisms of the immune system. Protein A is typically obtained by extraction from the cell wall of suitable *Staphylococcus aureus* strains, or preferably by isolation from the conditioned media of certain *Staphylococcus aureus* strains which secrete protein A. In either case, the protein A is normally affinity-purified to separate it from other proteins and contaminants. For example, the initial protein A preparation will be passaged over an affinity column having bound human IgG, which specifically binds to the protein A. The column is washed, and the bound protein A then eluted.

Protein A has found wide use in the selective purification of IgG from various biological samples. Additionally, protein A columns have recently been employed for the therapeutic removal of IgG and IgG-containing immune complexes in the treatment of certain cancers and autoimmune diseases. Such treatment protocols call for the removal of a volume of patient blood, separation of the blood into its plasma and cellular components, and perfusion of the plasma over a protein A column for removal of IgG and immune complexes. The cellular and treated plasma components are then reinfused into the patient, with the intention of stimulating the patient's immunne response.

While such protein A plasma perfusion therapies have enjoyed success, they have also been observed to induce certain toxic side effects in the treated patients, such as nausea, vomiting, fevers, chills, and the like. It is suspected that such toxic side effects may result from the presence of contaminating substances in the protein A compositions, particularly staphylococcal enterotoxins, which may leach from the adsorbant columns into the patient plasma during therapy.

The use of protein A as a direct immune system stimulant has also been investigated by injection of protein A into tumor-bearing animals. Although anti-tumor effects have been observed, significant toxic reactions have also been reported. Such toxic reactions appear to result from the presence of enterotoxins and other contaminants in the protein A.

It would therefore be desirable to provide purified protein A compositions and methods for preparing such compositions. In particular, it would be desirable to provide for protein A compositions which are substantially free from staphylococcal enterotoxins and other proteinaceous contaminants.

2. Description of the Background Art

Various reports have indicated that staphylococcal protein A preparations may be contaminated by trace amounts of staphylococcal enterotoxin(s) (Smith et al. (1983) J. Immunol. 130:773; Carlsson (1984) Cell. Immunol. 86:136; Schrezenmeier (1987) J. Immunol. Methods. 105:133). It has recently been suggested that the interferon-inducing capability of protein A derives from the presence of enterotoxin (Carlsson et al., supra.). Moreover, since enterotoxins are extremely potent mitogens, it has been proposed that the mitogenic effects observed with protein A may in fact be due to contamination by enterotoxins (Schrezenmeier et al., supra.). Ion exchange chromatography is a known technique for separating proteins. See, e.g., Hudson and Hay, *Practical Immunology*, 2nd. ed., Blackwell Scientific Publications, Oxford, 1980, pp. 169-175.

SUMMARY OF THE INVENTION

Protein A compositions are prepared having very low levels of trace contamination, typically being below about 10% by weight, usually being below about 5% by weight, and preferably being below about 2% by weight, more preferably being below about 1% by weight. In particular, the compositions are substantially free from staphylococcal enterotoxin B (SEB) and several other low molecular weight (less than 50 kD) proteinaceous contaminants, which have been found to be present in affinity-purified protein A preparations. Preferably, the protein A compositions of the present invention will have less than about 0.001% by weight SEB, more preferably being below about 0.0005% by weight, and most preferably being below about 0.00001% by weight.

In the method of the present invention, protein A is obtained from natural sources, such as enzyme-digested *Staphylococcus aureus* or conditioned media from *Staphylococcus aureus* cell culture, by affinity chromatography. The affinity-purified protein A is then contacted with an anionic exchange material under conditions which result in binding of the protein A together with the SEB and proteinaceous contaminants to the material. The SEB and proteinaceous contaminants are then selectively eluted from the anionic exchange material with a suitable low ionic strength buffer. The protein A is separately eluted with a higher ionic strength buffer, resulting in the high purity protein A composition of the present invention.

BRIEF DESCRIPTION OF THE DRAWINGS

FIG. 1 is a representative HPLC profile demonstrating the separation of protein A and SEB, as described in detail in the Experimental section hereinafter.

FIG. 2 is a chart illustrating the representative amounts of total protein (predominantly protein A) and SEB eluted from a DEAE-cellulose column with buffers having different ionic strengths, as described in greater detail in the Experimental section hereinafter.

FIG. 3 is a representative PAGE analysis of the SEB fraction eluted from the DEAE-cellulose ion exchange column with 0.005M NaCl, illustrating the dominant SEB peak, together with several lesser peaks, as described in more detail in the Experimental section hereinafter.

DESCRIPTION OF THE SPECIFIC EMBODIMENTS

Protein A may be obtained from virtually all Staphylococcus species which produce protein A, particularly from strains of *Staphylococcus aureus*, such as *S. aureus* Cowan I.

Depending upon the staphylococcal strain employed, the protein A will either remain fixed in the cell wall or will be secreted into the growth medium during cell growth. For strains which do not secrete, the protein A is recovered by enzyme digestion of the cell wall under conditions which release but do not degrade the protein. The digested cellular components may then be applied to a suitable affinity column, as described in more detail hereinbelow, by conventional techniques. A specific procedure for affinity-purifying protein A from a non-secreting staphylococcal strain is described in Sjoquist et al. (1972) Eur. J. Biochem. 29:572. For strains which secrete the protein A into the growth medium, the conditioned media may be applied directly to the affinity column for removal of the protein A. The recovery of protein A from such strains is described in greater detail in Lindmark et al. (1977) Eur. J. Biochem. 74:62. Generally, it will be preferred to employ staphylococcal strains which secrete the protein A into the growth media.

Conveniently, the conditioned media of a staphylococcal strain which secretes the protein A may be passaged over the affinity column to bind the secreted protein A. The affinity column will then be extensively washed to remove non-specifically bound proteins, typically with a buffer, such as phosphate buffered saline (PBS) at a pH of from about 7 to 8. The column will be washed until it appears that protein is no longer being released. Protein A may then be eluted from the column using an appropriate buffer, such as 0.1M glycine/HCl, at a pH of about 3. The eluted protein may then be collected and concentrated, typically using a molecular sieve having a suitable cut-off, e.g., 10 kD.

Affinity columns suitable for use in the initial purification step of protein A may comprise any receptor capable of specifically binding the protein A. The receptor will usually be IgG, more usually being human IgG, although a variety of other receptors, such as anti-protein A antibodies, may also find use. The receptor will be covalently bound to a suitable solid phase support, typically discrete particles, such as agarose beads, particulate silica, dextrans, and the like. Particularly suitable are human IgG-agarose matrices prepared by cyanogen bromide coupling, as described in Axen et al. (1967) Nature 214:1302.

Suitable affinity-purified protein A may also be obtained from a variety of commercial sources, such as Pharmacia, Inc., Piscataway, N.J.; Sigma Chemical Co., St. Louis, Mo.; Bio-Rad Laboratories, Inc., Hercules, Calif.; and Calbiochem Biochemicals, San Diego, Calif.

Affinity-purified protein A obtained as described above has been found to contain a significant level of proteinaceous contamination, including staphylococcal enterotoxins, particularly staphylococcal enterotoxin B (SEB), as well as several other low molecular weight (less than 50 kD) staphylococcal proteins. The reason for the presence of the contaminating staphylococcal proteins in the affinity-purified protein A preparations is not presently known. Such trace contamination may result from non-specific adsorption of the proteins to the IgG affinity column employed to isolate the protein A. Alternatively, small amounts of human antibodies to the proteins may be present in the IgG preparation bound to the affinity support matrix. In any event, it is necessary to remove these contaminants from the protein A compositions of the present invention.

SEB and other proteinaceous contaminants are removed from the affinity-purified protein A preparations by contacting such preparations with a suitable anionic ion exchange material. Such ion exchange material generally comprise the support matrix, having basic (anion exchange) groups attached thereto. The affinity-purified protein A is applied to the column under conditions which result in exchange between the anionic groups on the column matrix with anionic functionalities on the proteins, resulting in binding of the proteins, including the protein A, SEB, and other proteinaceous contaminants, to the column matrix. An elution buffer is then applied to the column, and by varying the ionic strength and pH of the buffer, the different proteins may be selectively removed from the matrix. It has been found that the SEB and other low molecular weight proteinaceous contaminants may be selectively eluted with a low anionic strength buffer, while the protein A is removed with a higher ionic strength buffer, resulting in a highly selective separation of the contaminants from the protein A.

A variety of anionic exchange materials may be employed. Preferred is the use of exchange matrices having anionic functionalities introduced, such as diethylaminoethyl (DEAE). Suitable matrices include cellulose, acrylamide, silica gel, and the like. DEAE matrices allow for binding of the protein A and proteinaceous contaminants under conditions of ionic strength and pH at which the proteins are stable, i.e., ionic strengths from about 0.001 to 0.005M NaCl and a pH in the range from about 6.5 to 8.5. Suitable DEAE-cellulose columns are available commercially from suppliers such as Whatman, Clifton, N.J.

The affinity-purified protein A preparations may be applied to the DEAE columns as follows. The columns are first washed and equilibrated with water. The affinity-purified preparations are dialyzed against water, and applied to the column in the substantial absence of salt (e.g., below about 0.001M NaCl, preferably below about 0.001M NaCl) and at a pH in the range from about 6.5 to 8.5. Under such conditions, the protein A and proteinaceous contaminants will bind to the column matrix.

After binding of the protein A and proteinaceous contaminants, the contaminants (including SEB) may be eluted with a low ionic strength buffer, typically about 0.001 to 0.005M NaCl and a phosphate buffer, at a pH of about 6.5 to 8.5. After the contaminants have been removed, the protein A may be released and separately collected using a higher ionic strength buffer, typically 0.05 to 0.5M NaCl in phosphate buffer, with a pH in the range from about 6.5 to 8.5.

The protein A recovered from the ion exchange column may then be concentrated, and either used directly or lyophilized for storage.

The following examples are offered by way of illustration, not by way of limitation.

EXPERIMENTAL

Materials and Methods

1 Isolation of Protein A Employing Affinity Chromatography with Immobilized Human IgG Protein A was isolated from the fermentation broth of a strain of Staphylococcus that secretes protein A into the growth medium using an affinity matrix prepared by covalently coupling purified human IgG (Sigma Chemical Corp., St. Louis, Mo.) to Sepharose® 4B (Sigma Chemical Corp., St. Louis, Mo.) employing cyanogen bromide as previously described (Axen et al. (1967) Nature 214:1302). The fermentation broth was passaged over the affinity column to bind the secreted protein A and the affinity matrix was extensively washed with 0.01M phosphate buffered saline, pH 7.5, until protein was no longer released from the affinity column. Bound protein A was then eluted with 0.1M glycine/HCl, pH 3.0, and the eluted protein A concentrated using a Millipore membrane (10,000 molecular weight cut-off) concentration system. The protein content of the concentrate was determined by adsorption at 275 nanometers with an extinction coefficient of 1.65, as previously described (Sjoquist et al. (1972) Eur. J. Biochem., 29:572).

2. ELISA for the Detection of Staphylococcus enterotoxin B (SEB)

An ELISA technique was employed to detect the presence of SEB in the fluid phase. A series of standard SEB concentrations of 0, 10, 25, and 50 nanograms SEB/ml were prepared by diluting a reference preparation of SEB obtained from Sigma Chemical Corp. (St. Louis, Mo.) with 0.005M NaCl containing 0.01M phosphate buffer, pH 7.5. For the ELISA, 200 μl of each standard and experimental sample solution were added to ProBind Assay microtiter plates (Becton Dickinson Labware, Lincoln Park, N.J.) in duplicate. The samples were incubated in the microtiter wells for 30 minutes at 25° C. All wells were washed 3 times with 250μl of a solution containing 1% bovine serum albumin (Sigma Chemicals, St. Louis, Mo.) in 0.01M phosphate buffered saline, pH 7.5 (BSA/PBS). After washing, 200 μl of BSA/PBS containing 10 μg of $F(ab')_2$ fragments of rabbit anti-SEB IgG antibody were added to each well and incubated for 30 minutes at 25° C. After incubation, all wells were washed 3 times and 200 μl of a 1/500 dilution of peroxidase conjugated F(ab')2 fragments of goat anti-rabbit IgG antibody were added to each well. All wells were incubated for 30 minutes at 25° C. After incubation, all wells were washed 3 times with 250 μl of BSA/PBS. After washing 200 μl of substrate were added to each well and incubated at 25° C. After appropriate color development, the reaction was stopped by transferring 150 μl from each well to another ProBind assay plate. Optical density readings at 492 nanometers were determined in an ELISA reader and a standard curve was developed relating the optical density readings to known concentrations of the SEB standard solutions. From this standard curve, the concentration of an experimental sample was determined. Typically, the sensitivity of the assay was 10 μg and the correlation coefficient of the standard curve was from 0.950 to 0.990.

3. High Pressure Liquid Chromatography (HPLC) Analysis of Protein A Preparations Affinity-purified protein A preparations were analyzed for homogeneity and purity by HPLC analysis, as follows. Protein A preparations were extensively dialyzed against $H_2O$ (both protein A and SEB are soluble in water) prior to analysis. Samples (200 μg) of protein A were mixed with 0.01M phosphate buffer, pH 3.5, and injected into a 300 sw molecular sizing HPLC column (Water Chromatography Division, Milford Mass.) equilibrated with 0.01M phosphate buffer, pH 3.5. A pH of 3.5 was employed because it was observed that this pH gave maximum resolution and separation of protein A and SEB preparations by reducing the nonspecific adsorption properties between the proteins and the silica based HPLC matrix. Samples were passaged through the HPLC column at a flow rate of 0.5 ml/minute, and 1.0 ml fractions were collected and immediately neutralized to a pH of 7.0 to 7.5. Samples passed through the HPLC column were also analyzed for adsorption properties at 280 nanometers employing a liquid chromatography spectrophotometer (Water Chromatography Division, Milford, Mass.), and areas under the various protein peaks were determined to assess purity employing a Hewlett Packard 3392A Integrator (Hewlett Packard Company, Avondale, Pa.).

4. DEAE-Cellulose Ion Exchange Chromatography

Protein A preparations isolated by affinity chromatography employing human IgG covalently bound to Sepharose® 4B were further processed by passage over DEAE-cellulose (diethylaminoethyl-cellulose) ion exchange columns (Whatman, DE52, Clifton, N.J.). The DEAE-cellulose was loaded into columns (3 cm diameter by 13 cm length) to an approximate bed volume of 50 ml. The columns were extensively washed and equilibrated with $H_2O$. One hundred milligram samples of protein A isolated by affinity chromatography and extensively dialyzed against water, as described above, were applied to the DEAE-cellulose columns. Two hundred ml fractions were then collected employing a stepwise system of increasing ionic strength buffer systems. Immediately after application of the protein A, a 200 ml fraction was collected employing elution with 0.005M NaCl in 0.01M phosphate buffer, pH 7.5. A second 200 ml fraction was then collected employing elution with 0.05M NaCl in 0.01M phosphate buffer, pH 7.5. A final 200 ml fraction was then collected employing elution with 0.5M NaCl in 0.01M phosphate buffer, pH 7.5. The protein content of each fraction was determined by the method of Lowry et al. (1951) J. Biol. Chem. 193:265, and the SEB content of each fraction, after extensive dialysis against $H_2O$, was determined employing the ELISA technique described above. In addition, after extensive dialysis against $H_2O$, all samples were concentrated by lyophilization.

5. Polyacrylamide Gel Electrophoresis (PAGE)

For analysis of proteins isolated by ion exchange chromatography, sodium dodecyl sulfate (SDS) PAGE was performed under reducing conditions in 7.5% SDS-polyacrylamide gels using the buffer systems of Laemmli (1970) Nature 227:680. The samples were mixed with buffer so that the final solutions contained 5M urea, 2% (wt/vol) SDS, 5% (vol/vol) 2-mercaptoethanol, 0.01% bromophenol blue, and heated for 1 minute at 100° C. before application to gels. After electrophoresis and staining with Coomassie Brilliant Blue, the gel lanes were scanned in an automatic scanning gel densitometer (Hoefer Scientific Instruments, San Francisco, Calif.).

RESULTS

1. Detection of Trace Quantities of SEB in Protein A Preparations

To determine if SEB could be separated from protein A isolated by affinity chromatography and detected after separation, affinity-purified protein A samples (200 μg) were subjected to HPLC analysis, as described above. A standard preparation was prepared by contamination with a known amount of SEB. Separation of protein A from SEB was found to be distinct under the conditions described in Materials and Methods. A representative HPLC profile of a known mixture of protein A and SEB is set forth in FIG. 1.

HPLC fractions suspected of containing SEB were pooled and neutralized to pH 7.5 by rapid addition of 4N NaOH. After neutralization, the pooled fractions were analyzed by the ELISA technique described above for the presence and quantity of SEB. SEB contamination was found in various affinity-isolated protein A samples ranging from 0.018% to 0.138%. The results are summarized in Table 1.

TABLE 1

Percent SEB Contamination in Various Protein A Preparations

| Sample | Total Nanograms SEB* | Percent SEB Contamination |
|---|---|---|
| 1 | 152.1 | 0.076% |
| 2 | 35.1 | 0.018% |
| 3 | 40.5 | 0.020% |
| 4 | 149.4 | 0.075% |
| 5 | 276.3 | 0.138% |
| 6 | 132.3 | 0.066% |
| 7 | 71.1 | 0.036% |

*Represents total nanograms in a 200 μg protein A sample.

2. Removal of Trace Quantities of SEB from Protein A Preparations

In an effort to remove trace amounts of SEB and other contaminating proteins from affinity-purified protein A preparations, DEAE-cellulose ion exchange chromatography was employed. Affinity-purified protein A preparations were dialyzed extensively against water and applied to DEAE-cellulose ion exchange column equilibrated with water. In a stepwise fashion, as described in Materials and Methods, proteins bound to the ion exchange matrix were eluted sequentially with 0.005M, 0.05M, and 0.5M NaCl in 0.01M phosphate buffer, pH 7.5. After elution, the protein content of each fraction was determined, and each fraction was assessed for the presence of SEB employing the described ELISA technique. As shown in FIG. 2, small quantities of total protein (open-bars) were detected in the 0.005M NaCl eluate; whereas, the majority of protein was detected in the 0.05M and 0.50M NaCl eluates. The SEB (open-bars), in contrast, was eluted predominantly in the 0.005M NaCl eluate, which contained only small quantities of total protein. These results indicate that the contaminating SEB in the affinity-purified protein A preparations could be removed by passage of the protein A preparation over DEAE-cellulose and elution with low ionic strength buffer.

3. Characterization of SEB and Protein A After Ion Exchange Chromatography

Each fraction eluted from the DEAE-cellulose column was frozen at −70° C. and concentrated by lyophilization. After lyophilization, each fraction was rehydrated in water and dialyzed extensively against water at 4° C. After dialysis, the protein content of each fraction was measured as described above. To assess the purity of the protein A present in the 0.05M and 0.5M NaCl eluates, each fraction was subjected to HPLC analyses and the area of the protein A peak integrated and analyzed for percent purity as described above. As shown in Table 2, relative to the protein A preparation before ion exchange chromatography, the 0.05M NaCl eluate fraction was observed to show the highest degree of purity.

Additional studies were then performed to characterize the SEB contained in the 0.005M NaCl eluate fraction. As shown in FIG. 3, PAGE analyses of the 0.005M NaCl eluate fraction revealed a series of polypeptides ranging in molecular weight from 45K to less than 25K. Moreover, the predominant polypeptide present corresponded to SEB, as confirmed by the ELISA technique described above.

TABLE 2

Percent Purity of Protein A Preparations Before and After DEAE Ion Exchange Chromatography

| Sample | Untreated* | 0.05 M NaCl Fraction | 0.50 M NaCl Fraction |
|---|---|---|---|
| 1 | 98% | 100% | 99% |
| 2 | 95% | 100% | 86% |
| 3 | 93% | 95% | 99% |
| 4 | 95% | 100% | 92% |
| 5 | 99% | 99% | 98% |
| 6 | 90% | 96% | 97% |
| 7 | 94% | 96% | 97% |
| 8 | 95% | 100% | 96% |
| | $\overline{X}$ = 95% | $\overline{X}$ = 98% | $\overline{X}$ = 96% |

*Untreated values represent purity before DEAE-cellulose ion exchange chromatography Although the foregoing invention has been described in some detail by way of illustration and example for purposes of clarity of understanding, it will be obvious that certain changes and modifications may be practiced within the scope of the appended claims.

What is claimed is:

1. A method for separating proteinaceous contaminants from an affinity-purified protein A preparation, said method comprising:
   contacting the affinity-purified protein A preparation with an anionic exchange material under conditions of ionic strength and pH selected to allow binding of protein A and proteinaceous contaminants to the material;
   selectively eluting the protein A and proteinaceous contaminants including enterotoxin B in different fractions from the anionic exchange material; and
   collecting the fractions composed predominantly of protein A.

2. A method as in claim 1, wherein the anionic exchange material is DEAE-cellulose.

3. A method as in claim 2, wherein the DEAE-cellulose is in a column and the affinity-purified protein A preparation is contacted by application to the column.

4. A method as in claim 3, wherein contacting is performed at a salt concentration of less than about 0.001M and at a pH in the range from about 6.5 to 8.5.

5. A method as in claim 4, wherein the proteinaceous contaminants including enterotoxin B are eluted with 0.001 to 0.005M NaCl buffer, pH 6.5 to 8.5 and the protein A is eluted with 0.05 to 0.5M NaCl buffer, pH 6.5 to 8.5.

6. A method of claim 1, wherein said affinity purified protein A preparation is affinity purified on an IgG affinity column.

7. A method for preparing a protein A composition substantially free from proteinaceous contaminants, said method comprising:

contacting a protein A preparation having proteinaceous contaminants with immobilized receptor specific for the protein A, whereby the protein A is bound to the receptor;

releasing the protein A from the receptor to form an affinity-purified protein A preparation;

contacting the affinity-purified protein A preparation with an anionic exchange material under conditions of ionic strength and pH selected to allow binding of the protein A and proteinaceous contaminants to the resin;

selectively eluting the protein A and proteinaceous contaminants in different fractions from the anionic exchange material; and collecting the fractions composed predominantly of protein A.

8. A method as inn claim 7 wherein the immobilized receptor for protein A is human IgG.

9. A method as in claim 8 wherein the human IgG is bound too agarose and contained in a column, said protein A preparation having proteinaceous contaminants being passed through the column.

10. A method as in claim 9, wherein the protein A is released from the human IgG-agarose column by elution with 0.1M glycine/HCl, pH 3.0.

11. A method as in claim 7, wherein the released protein A is concentrated prior to contact with the anionic exchange material.

12. A method as in claim 7, wherein the anionic exchange material is DEAE-cellulose.

13. A method as in claim 12, wherein the DEAE-cellulose is in a column and the affinity-purified protein A preparation is contacted by application to the column.

14. A method as in claim 13, wherein contacting is performed at a salt concentration of less than about 0.001M and at a pH in the range from about 6.5 to 8.5.

15. A method as in claim 14, wherein the proteinaceous contaminants are eluted with 0.001 to 0.005M NaCl buffer, pH 6.5 to 8.5 and the protein A is eluted with 0.05 to 0.5M NaCl buffer, pH 6.5 to 8.5.

* * * * *